US010832817B2

United States Patent
Allison et al.

(10) Patent No.: US 10,832,817 B2
(45) Date of Patent: Nov. 10, 2020

(54) COGNITIVE PASSIVE HEALTH MONITORING

(71) Applicant: International Business Machines Corporation, Armonk, NY (US)

(72) Inventors: Taylor F. Allison, Durham, NC (US); Al Chakra, Apex, NC (US); Michael R. Swenson, Salisbury, NC (US); Li-An Yu, Raleigh, NC (US)

(73) Assignee: International Business Machines Corporation, Armonk, NY (US)

( * ) Notice: Subject to any disclaimer, the term of this patent is extended or adjusted under 35 U.S.C. 154(b) by 323 days.

(21) Appl. No.: 15/483,156

(22) Filed: Apr. 10, 2017

(65) Prior Publication Data

US 2018/0293355 A1 Oct. 11, 2018

(51) Int. Cl.
*G16H 50/20* (2018.01)
*G16H 40/67* (2018.01)

(52) U.S. Cl.
CPC .............. *G16H 50/20* (2018.01); *G16H 40/67* (2018.01)

(58) Field of Classification Search
CPC . G06F 19/00; G06F 17/30; A61B 5/00; A61B 1/08; G16H 50/20; G16H 40/67; G06N 5/04
USPC ............................ 705/2, 3; 707/737; 702/188
See application file for complete search history.

(56) References Cited

U.S. PATENT DOCUMENTS

| 7,001,334 B2 * | 2/2006 | Reed ................... A61B 5/0002 600/300 |
| 7,141,026 B2 * | 11/2006 | Aminian ............... A61B 5/1116 600/595 |
| 9,357,921 B2 | 6/2016 | Chang et al. |
| 9,811,818 B1 * | 11/2017 | Xing ................... A61B 10/0051 |
| 10,170,153 B2 * | 1/2019 | Ekambaram ......... G11B 27/005 |
| 2005/0197539 A1 * | 9/2005 | Choate .................... A61B 5/00 600/300 |

(Continued)

FOREIGN PATENT DOCUMENTS

WO WO-2012170584 A1 * 12/2012 ........... A61B 5/0022

OTHER PUBLICATIONS

Hassanalieragh, M. et al. Health monitoring and management using internet-of-things (IoT) sensing with cloud-based processing: Opportunities and challenges. 2015 IEEE International Conference on Services Computing, IEEE Computer Society, 2015, pp. 285-292.

(Continued)

*Primary Examiner* — Aryan E Weisenfeld
*Assistant Examiner* — Alaaeldin M Elshaer
(74) *Attorney, Agent, or Firm* — Ingrid M. Foerster; Edell, Shapiro & Finnan, LLC

(57) ABSTRACT

A method, computing system and computer program product are provided. A group of connected devices are formed from at least some multiple connected devices. A computing system receives current usage data for a person from the group of connected devices with respect to activities. The computing system compares the current usage data with a baseline for the person to produce change data and applies an analytic analysis to the change data to determine a health concern for the person. A notification is provided when the change data exceeds a predetermined threshold with respect to the baseline. In another embodiment, a group of connected devices is managed by excluding, from the group, a connected device that contributes to false positive data.

8 Claims, 4 Drawing Sheets

(56) References Cited

U.S. PATENT DOCUMENTS

| | | | | |
|---|---|---|---|---|
| 2008/0133297 | A1* | 6/2008 | Schmotzer | G06F 19/3481 705/7.27 |
| 2008/0284592 | A1* | 11/2008 | Collins, Jr. | G08B 21/0423 340/541 |
| 2011/0046498 | A1* | 2/2011 | Klap | A61B 5/0205 600/534 |
| 2011/0213216 | A1* | 9/2011 | McKenna | A61B 5/0002 600/301 |
| 2011/0245633 | A1* | 10/2011 | Goldberg | A61B 5/681 600/301 |
| 2014/0364771 | A1* | 12/2014 | Pitts | A61B 5/6885 600/595 |
| 2015/0019553 | A1* | 1/2015 | Shaashua | H04W 4/70 707/737 |
| 2015/0095054 | A1* | 4/2015 | Kaigler | G06F 19/3418 705/2 |
| 2016/0084869 | A1* | 3/2016 | Yuen | G01P 7/00 73/510 |
| 2016/0139680 | A1* | 5/2016 | Noorzai | G06F 3/0231 345/168 |
| 2017/0177811 | A1* | 6/2017 | McFarland | G16H 40/40 |
| 2017/0245806 | A1* | 8/2017 | Elhawary | G06F 19/3481 |
| 2018/0000416 | A1* | 1/2018 | Hegde | A61B 5/6805 |
| 2018/0039745 | A1* | 2/2018 | Chevalier | G16H 10/60 |
| 2019/0008463 | A1* | 1/2019 | Xing | |

OTHER PUBLICATIONS

Haque, S. A., Rahman, M., & Aziz, S. M. (2015). Sensor anomaly detection in wireless sensor networks for healthcare. Sensors, 15(4), 8764-8786.

Gómez, J., Oviedo, B., & Zhuma, E. Patient Monitoring System Based on Internet of Things. Procedia Computer Science 83, 2016, pp. 90-97.

LeWine, H. Grip strength may provide clues to heart health. Harvard Health Blog. http://www.health.harvard.edu/blog/grip-strength-may-provide-clues-to-heart-health-201505198022. Retrieved from internet Jan. 2017, 3 pages.

* cited by examiner

COGNITIVE PASSIVE HEALTH MONITORING

BACKGROUND

Present invention embodiments are related to systems, methods and computer program products for collecting data received from a number of objects that are frequently used by a person, detecting a health concern based on the collected data, and providing a notification when the health concern is detected. In particular, present invention embodiments are related to systems, methods and computer program products for collecting movement-related data from a group of objects that are frequently used by a person, comparing the movement-related data with a baseline of movement-related data associated with the person to produce change data, applying an analytic analysis to the change data to determine a health concern, and providing a notification when at least a predetermined variation is detected for at least a specific period of time.

Many people are diagnosed with unexpected health concerns every day. Some are surprised to learn of their health concern because any discomfort they experience may be minor, at least at a start of a health problem, and they may be distracted. Others may be unable to communicate their discomfort due to being very young, due to a form of dementia or due to other cognitive issues.

For example, a person walks into another room, picks up a toothbrush to brush his or her teeth, and combs his or her hair as part of their daily routine for getting ready for the day ahead. If the person is experiencing pain or discomfort such as, for example, pain in his or her right shoulder (assuming the person is right-handed), these tasks may be altered. By way of example, the person may not hold the toothbrush in a usual manner or comb his or her hair using a different movement than as usual. The pain or discomfort may get worse each day for several days until finally, the person stops using his or her dominant hand. In addition, some tasks take an increasing amount of time to complete. These alterations may indicate that the person is experiencing shoulder pain.

SUMMARY

In a first aspect of the invention, a machine-implemented method is provided for monitoring activities and identifying health concerns. A group of connected devices may be formed from at least some multiple connected devices. Current usage data for a person may be received by a computing system from the group of connected devices with respect to the activities. The computing system may compare the current usage data with a baseline for the person to produce change data and may apply an analytic analysis to the change data to determine a health concern for the person. The computing system may provide a notification when the change data exceeds a predetermined threshold with respect to the baseline.

In a second aspect of the invention, a computing system for monitoring activities and identifying health concerns is provided. The computing system includes at least one processor, a memory to store data and instructions for the at least one processor, a network adaptor to communicate with multiple connected devices, and a communications bus that connects the at least one processor with the memory and the network adaptor. The at least one processor is configured to perform: forming a group of connected devices from at least some multiple connected devices; receiving current usage data for a person from the group of connected devices with respect to the activities; comparing the current usage data with a baseline for the person to produce change data; applying an analytic analysis to the change data to determine a health concern for the person; and providing a notification when the change data exceeds a predetermined threshold with respect to the baseline.

In a third aspect of the invention, a computer program product is provided. The computer program product includes at least one computer readable storage medium having computer readable program code embodied therewith for execution on at least one processor, wherein the computer readable program code is configured to be executed by the at least one processor to perform: forming a group of connected devices from at least some multiple connected devices; receiving current usage data for a person from the group of connected devices; comparing the current usage data with a baseline to produce change data; applying an analytic analysis to the change data to determine a health concern for the person; and providing a notification when the change data exceeds a predetermined threshold with respect to the baseline.

BRIEF DESCRIPTION OF THE DRAWINGS

Generally, like reference numerals in the various figures are utilized to designate like components.

DETAILED DESCRIPTION

Figure 1:
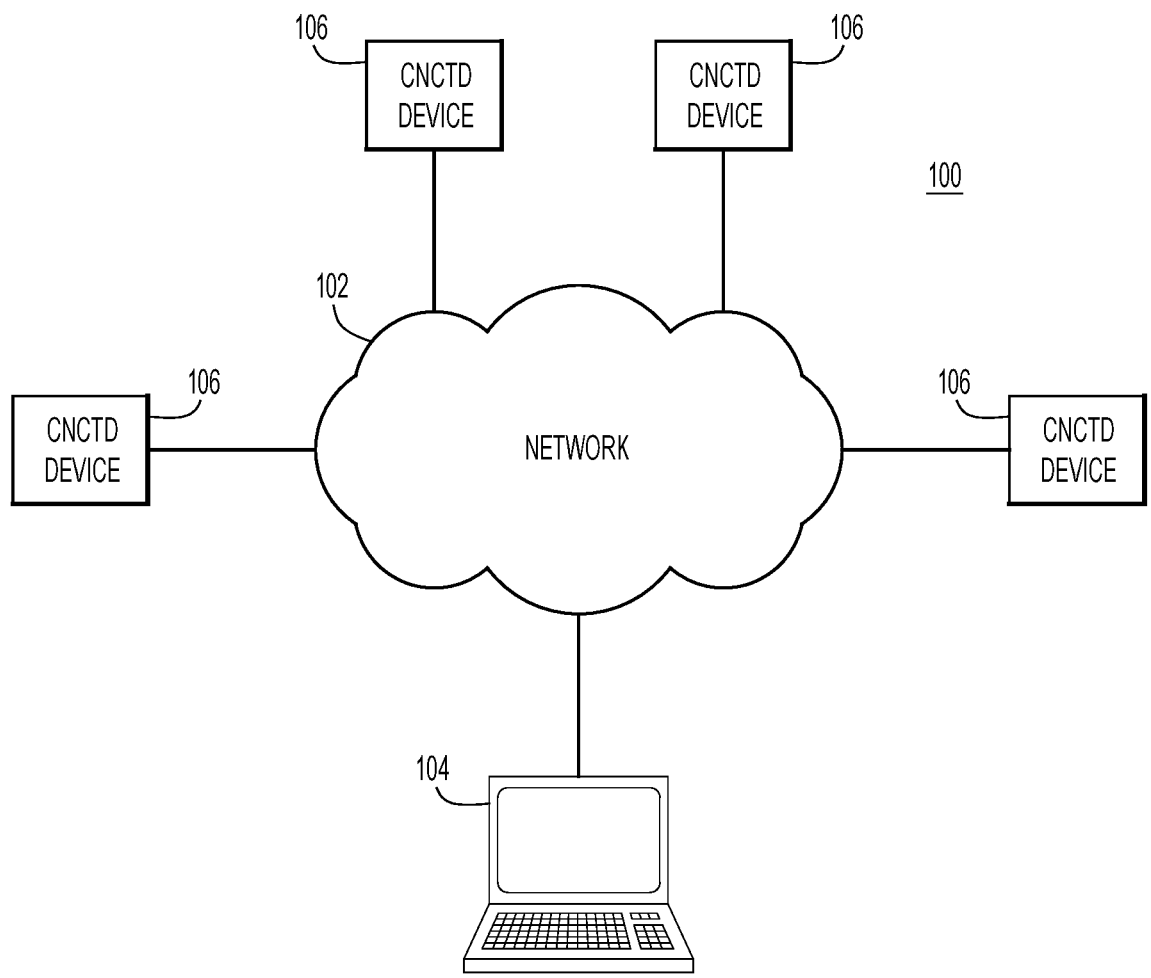
FIG. 1 illustrates an example environment in which various embodiments may be implemented.

Present invention embodiments include methods, systems and computer program products for receiving data from a number of connected or networked objects that a person uses regularly. In various embodiments, the objects may be Internet of Things (IoT) devices that measure and report a number of metrics associated with the person. The objects may include, but not be limited to, a comb, a toothbrush, a shaving kit, a doorknob, etc.

Present embodiments receive a history of usage data associated with a person from multiple connected devices. Each of the multiple connected devices may have information stored therein regarding a user's identity and may make a number of measurements while the user uses each of the multiple connected devices. The measurements may include, but not be limited to, an amount of pressure applied, whether a right hand or a left hand is used, a direction of movement, a number of strokes, a type of motion, and a total amount of time for performing a task. Each of the multiple connected devices may report the measurements (also referred to as usage data) to a computing system. The computing system may receive and store the usage data over a period of time such as, for example, 3 days, one week, one month, or another suitable time period. The usage data that are received and stored over the period of time may be referred to as a history of usage data.

A first analytic analysis may be applied to the history of usage data to form a baseline for the person. The baseline may include, but not be limited to, a timeline, movement information, whether a right hand or a left hand was used, and a total time for performing a task. A group of connected devices may be formed from at least some of the multiple connected devices. The computing system may receive current usage data for the person from the group of connected devices while the user uses each of the connected devices of the group of connected devices. The computing system may then compare the received current usage data from each of the connected devices to the baseline to produce change data indicating an amount of change in each of the measurements from each of the devices with respect to the baseline. A second analysis may be applied to the change data to determine a health concern for the person. The second analysis may analyze the change data from each of the connected devices of the group, separately and in combination, to make a number of determinations including, but not limited to, which hand was used, an amount of pressure applied, a direction of movement, a total time for performing a task, and a type of motion such as, for example, circular, back and forth, up and down, etc.

When the second analysis determines a change in the change data that exceeds a predetermined variation from the baseline, an anomaly is suspected and data concerning the suspected anomaly may be saved in a possible anomaly repository. The data concerning the suspected anomaly from a connected device may be compared with the data collected from one or more other connected devices of the group and results of the comparing may be stored in the possible anomaly repository. If the second analysis determines that the change data exceeds the predetermined variation from the baseline for consecutive measurements over a predetermined time period, then a notification may be provided.

If the second analysis determines that the change data exceeds the predetermined variation from the baseline, but does not exceed the predetermined variation for a duration of the predetermined time period, then the computing system may access usage data associated with one or more other persons with similar characteristics including, but not limited to, being in a same age group, having a height and a weight within a predetermined variation of a height and a weight of the person, as well as other similar characteristics. The usage data associated with the one or more other persons may be compared to the usage data associated with the person to determine whether the usage data associated with the one or more other persons has a similar pattern of anomalies and possible anomalies. When the similar pattern of anomalies and the possible anomalies is determined, an occurrence of an anomaly may be recorded and a notification regarding a health concern for the person may be provided.

FIG. 1 shows an example environment 100 in which various embodiments may be implemented. Example environment 100 may include a network 102, a computing system 104 and a number of connected devices 106. In some embodiments, the connected devices may be Internet of Things (IoT) devices that are wirelessly connected to network 102. Network 102 may include a local area network (LAN), a wide area network (WAN), a public switched data network (PSDN), the Internet, an intranet, other types of networks, or any combination of the above. Computing system 104 may have access to a relational database management system (not shown), which may be local or remote with respect to computing system 104. Further, in some embodiments, computing system 104 may include a server or a group of servers such as a server farm. Computing system 104 and connected devices 106 may communicate with each other via network 102.

Figure 2:
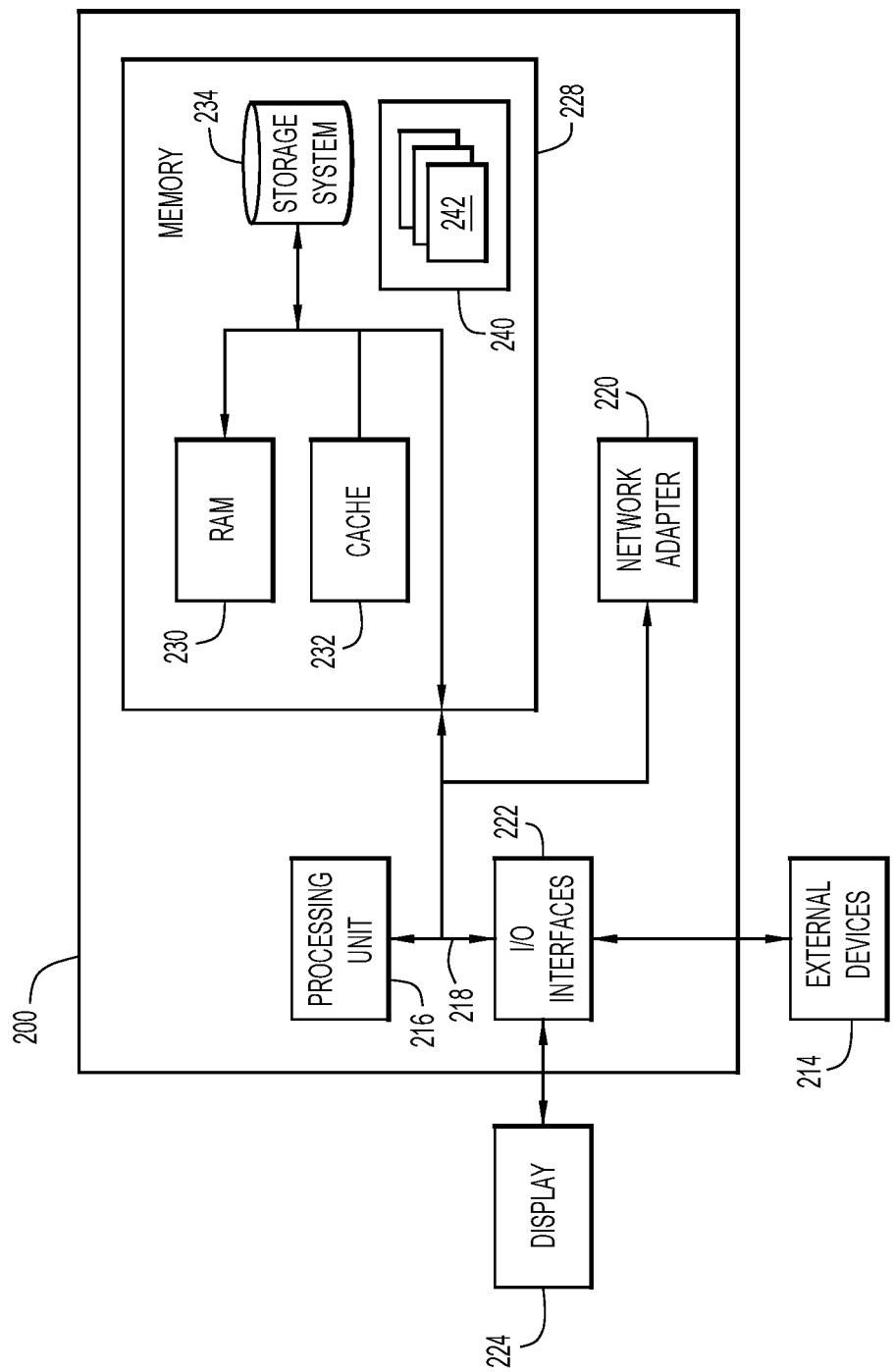
FIG. 2 is a functional block diagram of an example computing system that may implement various embodiments of the invention.

Computing system 104 and connected devices 106 may each be implemented by computing system 200 shown in FIG. 2. Computing system 200 is shown in a form of a general-purpose computing device. Components of computing system 200 may include, but are not limited to, one or more processors or processing units 216, a system memory 228, and a bus 218 that couples various system components including system memory 228 to one or more processors 216. When computing system 200 implements connected devices 106, computing system 200 may further include a number of sensors (not shown) connected to bus 218 for sensing and generating data concerning movements, an orientation, an amount of pressure applied, a hand being used to hold a connected device, a speed of movement, an amount of time for performing a series of movements, etc.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computing system 200 typically includes a variety of computer system readable media. Such media may be any available media that is accessible by computing system 200, and may include both volatile and non-volatile media, removable and non-removable media.

System memory 228 can include computer system readable media in the form of volatile memory, such as random access memory (RAM) 230 and/or cache memory 232. Computing system 200 may further include other removable/non-removable, volatile/non-volatile computer system storage media. By way of example only, storage system 234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and the program data or some combination thereof, may include an implementation of a networking environment. Program modules 242 generally carry out the functions and/or methodologies of embodiments of the invention as described herein.

Computing system 200 may also communicate with one or more external devices 214 such as a keyboard, a pointing device, a display 224, etc.; one or more devices that enable a user to interact with computing system 200; and/or any devices (e.g., network card, modem, etc.) that enable computing system 200 to communicate with one or more other computing devices. Such communication can occur via Input/Output (I/O) interfaces 222. Still yet, computing system 200 can communicate with one or more networks such as a local area network (LAN), a general wide area network (WAN), and/or a public network (e.g., the Internet) via network adapter 220. As depicted, network adapter 220 communicates with the other components of computing system 200 via bus 218. It should be understood that, although not shown, other hardware and/or software components could be used in conjunction with computing system 200. Examples, include, but are not limited to: microcode, device drivers, redundant processing units, external disk drive arrays, RAID systems, tape drives, and data archival storage systems, etc.

Figure 3:
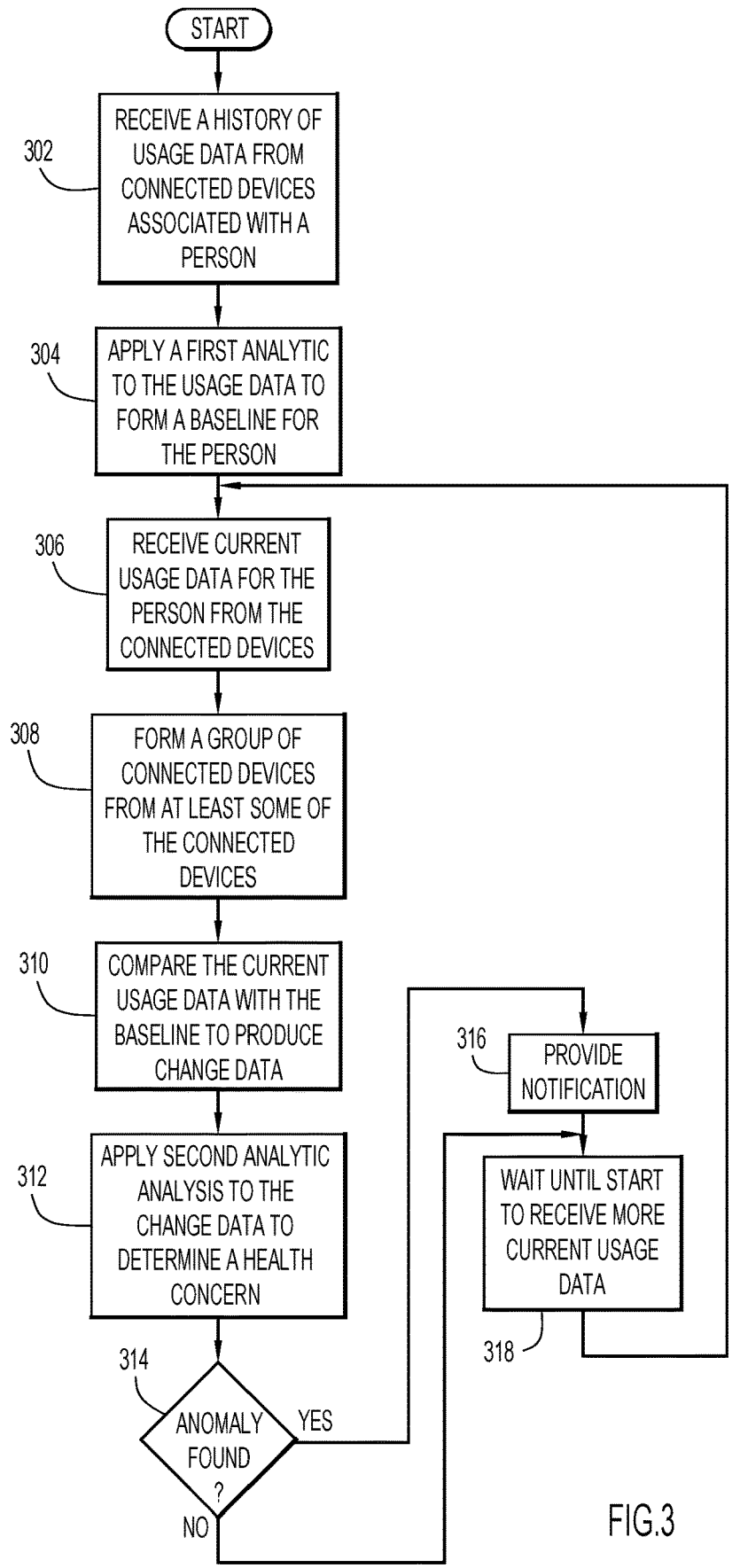
FIG. 3 is a flowchart that illustrates example processing regarding receiving usage data from connected devices, analyzing the usage data and determining whether a health concern exists according to an embodiment of the present invention.

FIG. 3 is a flowchart that illustrates example processing that may be performed by computing system 104 in various embodiments. The process assumes that a user of the connected devices elected to have his or her usage of the connected devices monitored. The process may begin with receiving a history of usage data from a number of connected devices (act 302). In various embodiments, the connected devices may be IoT devices including, but not limited to, a comb, a hairbrush, a toothbrush, a doorknob, an electric shaver and a manual razor. The history of usage data may be collected over a predefined period of time such as, for example, one month, two weeks, one week, five days or another suitable time and may be associated with a single person who is known to be in a healthy condition. The usage data may include, but not be limited to at least one of: an amount of pressure applied, a direction of movement, a number of strokes, whether a right hand or a left hand is used, a total amount of time for performing a task, and a type of motion such as up-and-down, side to side, circular or other type of motion.

A first analytic analysis may be applied to the usage data to form a baseline for the person (act 304). The baseline may include information such as at least one of: whether a right hand or a left hand is used, an average amount of pressure applied (or, alternatively, a range of amounts of pressure applied), a direction of movement, an average number of strokes (or, alternatively, a range of a number of strokes), an average or a mean time for performing a task, a type of motion such as circular, side-to-side, up and down, and diagonally, and other usage data.

After a baseline is formed for the person, as the person goes about using the connected devices, computing system 104 may receive usage data from at least some of the number of connected devices (act 306). Computing system 104 may form a group of connected devices from one or more of the at least some of the number of connected devices (act 308). For example, the person may wake in the morning, walk to a door and use a doorknob to enter a room. The doorknob may measure an amount of pressure applied by the person, may determine whether a right hand or a left hand is used and a direction in which the doorknob is turned, and may send usage data, including the above measurements and determinations, to computing system 104. The person may enter the room and may brush his or her teeth. The toothbrush may measure an amount of pressure applied by the person, may determine whether the person is brushing with a right hand or a left hand, may determine a type of motion and may send usage data including the above-mentioned measurements and determinations to computing system 104. The person may then use a comb to comb his or her hair. The comb may make measurements and determinations similar to those described above with respect to the toothbrush and may provide the measurements and determinations as usage data to computing system 104.

As computing system 104 receives current usage data from the multiple connected devices, computing system 104 may form a group of connected devices based on the multiple connected devices that are providing the current usage data. Computing system 104 may then compare the current usage data from the group of connected devices to the baseline to produce change data (act 310), which indicates an amount of change of various measurements with respect to the baseline. The change data may also provide other information such as, a change from using a right hand to a left hand and vice versa, a change in a type of movement when performing a specific task, a change in an amount of time to complete a task, etc. Computing system 104 may apply a second analytic analysis to the change data to determine a health concern (act 312).

Figure 4:
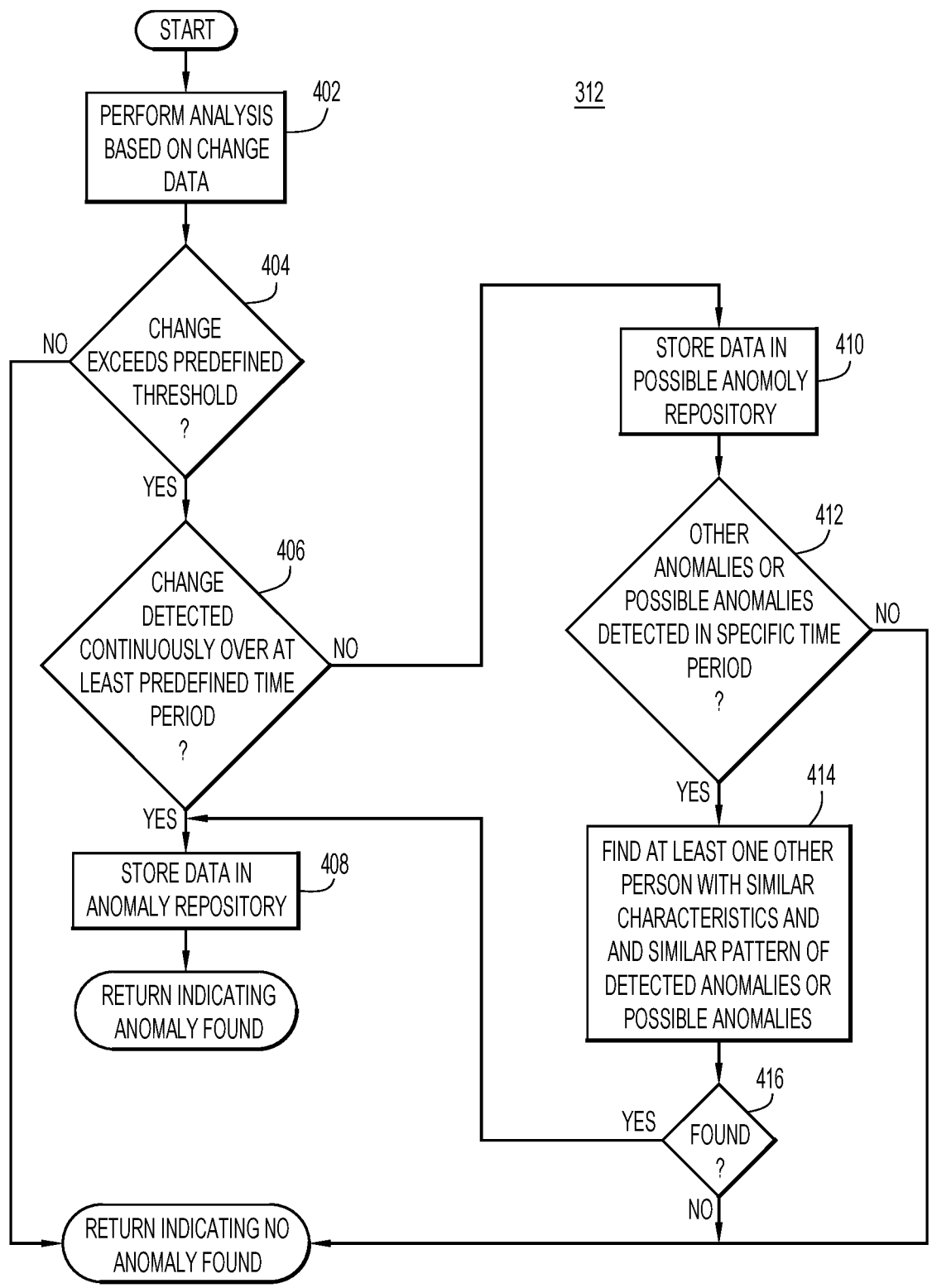
FIG. 4 is a flowchart illustrating example processing regarding determining whether a health concern exists based on the received usage data according to an embodiment of the present invention.

FIG. 4 is a flowchart of act 312 from FIG. 3. Computing system 104 may perform the second analytic analysis based on the change data (act 402). A determination may be made regarding whether an amount of change of any of the change data exceeds a predefined threshold (act 404). In some embodiments, the predefined threshold may be 5% or another value. If the amount of change of all of the change data does not exceed the predefined threshold, then the process returns to a calling process and indicates that an anomaly was not found. Otherwise, computer system 104 may determine whether the change data exceeded the predefined threshold continuously over at least a predefined time period (act 406). The predefined time period may be three consecutive days, five consecutive days, or another suitable predefined time period.

If the change data exceeds the predefined threshold continuously for at least the predefined time period, then the change data may be stored in an anomaly repository (act 408) and the process may indicate that an anomaly was found.

If, during act 406, a determination was made that the change data did not exceed the predefined threshold for at least the predefined time period, then data concerning a possible anomaly may be stored in a possible anomaly repository (act 410). Computing system 104 may then examine the anomaly repository and the possible anomaly repository to determine whether any anomalies or possible anomalies were detected during a specific time period such as, for example, three days, one week, or another time period (act 412). If no anomalies or possible anomalies were detected within the specific time period, then the process may indicate that no anomaly was found.

If, during act 412, at least one other anomaly or possible anomaly was detected within the specific time period, then usage data associated with at least one other person having characteristics (height, weight, age, etc.) similar to the person may be analyzed to determine an existence of a similar pattern of detected anomalies or possible anomalies (act 414). If the similar pattern of detected anomalies or possible anomalies is determined to exist with respect to the at least one other person, then anomaly data may be stored in the anomaly repository (act 408) and the process may indicate that an anomaly is found. Otherwise, the process may indicate that no anomaly was found.

Returning to FIG. 3, a determination is made regarding whether an anomaly is found (act 314). If the anomaly is found, then a notification may be provided (act 316). The notification may indicate a specific health concern (e.g., shoulder pain, etc.) and may be provided to the person, the person's caregiver, the person's doctor, the person's health coach, or other person associated with the person. The notification may be made via an email message, a text message, a phone call, a voice message, or via another method. In one embodiment, in addition to, or instead of, providing the notification, computing system 104 may schedule an appointment for the person with a healthcare provider.

Computing system 104 may then wait until more current usage data is received (act 318), at which point, the current usage data for the person is received from the group of connected devices (act 306).

In some embodiments, the second analytic analysis may determine that current usage data from one or more connected devices of the group of connected devices is irrelevant or unreliable regarding the second analytic analysis. In such a situation, the one or more connected devices may be excluded from the group of connected devices. Further, a user may exclude any of the connected devices from the group of connected devices via any one of a number of methods including, but not limited to, pressing a button or actuating a switch on a respective connected device, logging in to computing system 104 and indicating a desire to exclude the one or more connected devices via a user interface, or via other methods.

Similarly, computing system 104 may add a connected device to a group of connected devices upon detecting the connected device, upon detecting activation of a switch on the connected device by a user, after the user logs in to computing system 104 and indicates a desire to add the connected device to the group of connected device via a user interface, or via other methods.

In an alternative embodiment, before a baseline is established usage data may be collected and stored within each connected device for at least a predefined period of time, during which a person who uses the connected devices is known or assumed to be healthy. Each of the connected devices may perform a first analytic analysis to form a baseline for the person with respect to each of the connected devices and the baseline from each of the connected devices may then be provided to computing system 104, which receives the baseline from each of the connected devices. After computing system 104 receives the baseline for each of the multiple connected devices, acts 306 through 308 may be performed by computing system 104 as previously described.

The environment of present invention embodiments may include any number of computers or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and may communicate via any suitable communications medium (e.g., LAN, WAN, Intranet, Internet, hardwired, modem connection, wireless, etc.). For example, the functions of the present invention embodiments may be distributed in any manner among the various systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to a server and/or client systems. The database systems and/or storage structures may be remote from or local to the computer or other processing systems, and may store any desired data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

We claim:

1. A machine-implemented method for monitoring activities and identifying health concerns, the machine-implemented method comprising:
   receiving, by a computing system connected to a network from a plurality of connected devices connected to the network, measurements with respect to the activities of a person while the person uses each of the plurality of connected devices, the plurality of connected devices being wirelessly connected to the network, the each of the plurality of connected devices being an object that is handheld by the person when in active use by the person, actively used by the person on a regular basis and includes a plurality of sensors for generating the measurements including movement-related measurements with respect to the active use of the object by the person, the movement-related measurements including an amount of pressure applied by a hand, a direction of movement, a number of strokes, a type of motion, whether a right hand or a left hand is being used, and a total amount of time for performing a task;
   comparing, by the computing system, the movement-related measurements with a baseline of movement-related measurements associated with the person to produce change data indicating an amount of change with respect to the baseline, the baseline having been produced by analyzing a history of measurements for a predefined period of time, the history of measurements being associated with the person and including the movement-related measurements with respect to active use of the plurality of connected devices by the person, the movement-related measurements included in the history of measurements being originally generated and provided by the plurality of sensors included in the plurality of connected devices regularly used by the person when the person was known to be in a healthy condition;
   analyzing, by the computing system, the change data to determine a health concern for the person based, at least partly, on an amount of change of the measurements from the baseline as indicated by the change data;
   performing, by the computing system, responsive to detecting that the amount of change continuously exceeds a predefined threshold for at least a predefined amount of time:
      storing the change data in a first repository for anomaly data, and
      providing a notification regarding the person;
   performing, by the computing system in response to determining that the amount of change exceeds the predefined threshold, but fails to continuously exceed the predefined threshold for at least the predefined amount of time:
      storing data concerning a possible anomaly in a second repository for possible anomaly data,
      examining the first repository and the second repository to determine whether one of any anomalies and any possible anomalies was detected within a specific time period, and
      performing, responsive to determining that the one of the any anomalies and the any possible anomalies was detected:
         determining whether usage data of at least one other person with characteristics within a predetermined variation of characteristics of the person has a pattern of one of detected anomalies and detected possible anomalies within a predefined variation of a pattern of the one of the any anomalies and the any possible anomalies of the person detected within the specific time period, and
         performing, responsive to determining that the at least one other person has the pattern within the predefined variation of the pattern of the person:
            storing anomaly data in the first repository, and
            providing the notification indicating that an anomaly was detected regarding the person.

2. The machine-implemented method of claim 1, wherein the change data includes movement aspects regarding a dominant hand used.

3. The machine-implemented method of claim 1, wherein the group of connected devices includes a plurality of Internet of Things devices that the person uses on a regular basis.

4. A computer system for monitoring activities and identifying health concerns, the computer system comprising:
   at least one processor;
   a memory to store data and instructions for the at least one processor;
   a network adaptor to communicate with a plurality of connected devices;
   and a communication bus connecting the at least one processor with the memory and the network adaptor, wherein the at least one processor is configured to perform:
   receiving, via a network from a plurality of connected devices, measurements with respect to the activities of a person while the person uses each of the plurality of connected devices wirelessly connected to the network, the each of the plurality of connected devices being an object that is handheld by the person when in active use by the person, actively used by the person on a regular basis and includes a plurality of sensors for generating the measurements including movement-related measurements with respect to the active use of the object by the person, the movement-related measurements including an amount of pressure applied by a hand, a direction of movement, a number of strokes, a type of motion, whether a right hand or a left hand is being used, and a total amount of time for performing a task;

comparing the movement-related measurements with a baseline of movement-related measurements associated with the person to produce change data indicating an amount of change with respect to the baseline, the baseline having been produced by analyzing a history of measurements for a predefined period of time, the history of measurements being associated with the person and including the movement-related measurements with respect to active use of the plurality of connected devices by the person, the movement-related measurements included in the history of measurements being originally generated and provided by plurality of sensors included in the plurality of connected devices regularly used by the person when the person was known to be in a healthy condition;

analyzing the change data to determine a health concern for the person based, at least partly, on an amount of change of the measurements from the baseline as indicated by the change data;

performing, responsive to detecting that the amount of change continuously exceeds a predefined threshold for at least a predefined amount of time:
  storing the change data in a first repository for anomaly data, and
  providing a notification regarding the person;

performing, in response to determining that the amount of change exceeds the predefined threshold, but fails to continuously exceed the predetermined threshold for at least the predefined amount of time:
  storing data concerning a possible anomaly in a second repository for possible anomaly data,
  examining the first repository and the second repository to determine whether one of any anomalies and any possible anomalies was detected within a specific time period, and
  performing, responsive to determining that the one of the any anomalies and the any possible anomalies was detected:
    determining whether usage data of at least one other person with characteristics within a predetermined variation of characteristics of the person has a pattern of one of detected anomalies and detected possible anomalies within a predefined variation of a pattern of the one of the any anomalies and the any possible anomalies of the person detected within the specific time period, and
    performing, responsive to determining that the at least one other person has the pattern within the predefined variation of the pattern of the person:
      storing anomaly data in the first repository, and
      providing the notification indicating that an anomaly was detected regarding the person.

5. The computer system of claim 4, wherein the change data includes movement aspects regarding a dominant hand used.

6. The computer system of claim 4, wherein the group of connected devices includes a plurality of Internet of Things devices that the person uses on a regular basis.

7. A computer program product for monitoring activities and identifying health concerns, the computer program product comprising:

at least one computer readable storage medium having computer readable program code embodied therewith for execution on at least one processor, the computer readable program code being configured to be executed by the at least one processor to perform:

receiving, via a network from a plurality of connected devices, measurements with respect to the activities of a person while the person uses each of the plurality of connected devices wirelessly connected to the network, the each of the plurality of connected devices being an object that is handheld by the person when in active use by the person, actively used by the person on a regular basis and includes a plurality of sensors for generating the measurements including movement-related measurements with respect to the active use of the object by the person, the movement-related measurements including an amount of pressure applied by a hand, a direction of movement, a number of strokes, a type of motion, whether a right hand or a left hand is being used, and a total amount of time for performing a task;

comparing the movement-related measurements with a baseline of movement-related measurements associated with the person to produce change data indicating an amount of change with respect to the baseline, the baseline having been produced by analyzing a history of measurements for a predefined period of time, the history of measurements being associated with the person and including the movement-related measurements with respect to active use of the plurality of connected devices by the person, the movement-related measurements included in the history of measurements being originally generated and provided by the plurality of sensors included in the plurality of connected devices regularly used by the person when the person was known to be in a healthy condition;

analyzing the change data to determine a health concern for the person based, at least partly, on an amount of change of the measurements from the baseline as indicated by the change data;

performing, responsive to detecting that the amount of change continuously exceeds a predefined threshold for at least a predefined amount of time:
  storing the change data in a first repository for anomaly data, and
  providing a notification regarding the person;

performing, in response to determining that the amount of change exceeds the predefined threshold, but fails to continuously exceed the predetermined threshold for at least the predefined amount of time:
  storing data concerning a possible anomaly in a second repository for possible anomaly data,
  examining the first repository and the second repository to determine whether one of any anomalies and any possible anomalies was detected within a specific time period, and
  performing, responsive to determining that the one of the any anomalies and the any possible anomalies was detected:
    determining whether usage data of at least one other person with characteristics within a predetermined variation of characteristics of the person has a pattern of one of detected anomalies and detected possible anomalies within a predefined variation of a pattern of the one of the any anomalies and the any possible anomalies of the person detected within the specific time period, and performing, responsive to determining that the at least one other person has the pattern within the predefined variation of the pattern of the person: storing anomaly data in the first repository, and providing the notification indicating that an anomaly was detected regarding the person.

8. The computer program product of claim 7, wherein the change data includes movement aspects regarding a dominant hand used.

* * * * *